US009481747B2

(12) United States Patent
Park et al.

(10) Patent No.: US 9,481,747 B2
(45) Date of Patent: Nov. 1, 2016

(54) OLEFIN-BASED POLYMER

(71) Applicant: LG CHEM, LTD., Seoul (KR)

(72) Inventors: Sang Eun Park, Daejeon (KR); Hae Woong Park, Daejeon (KR); Young Woo Lee, Daejeon (KR); Choong Hoon Lee, Daejeon (KR); Don Ho Kum, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 14/413,076

(22) PCT Filed: Sep. 25, 2014

(86) PCT No.: PCT/KR2014/008987
§ 371 (c)(1),
(2) Date: Jan. 6, 2015

(87) PCT Pub. No.: WO2015/046932
PCT Pub. Date: Apr. 2, 2015

(65) Prior Publication Data
US 2016/0272743 A1 Sep. 22, 2016

(30) Foreign Application Priority Data
Sep. 26, 2013 (KR) .................. 10-2013-0114253

(51) Int. Cl.
B01J 31/12 (2006.01)
C08F 210/16 (2006.01)
C08L 23/08 (2006.01)

(52) U.S. Cl.
CPC .......... *C08F 210/16* (2013.01); *C08L 23/0815* (2013.01); *C08L 2205/025* (2013.01)

(58) Field of Classification Search
CPC .... B01J 31/12; B01J 31/143; B01J 31/2295; B01J 2531/46; B01J 2531/48; C07F 7/28; C08F 10/00; C08F 210/16; C08F 4/65908; C08F 4/65912; C08F 4/6592; C08F 2420/06; C08F 2500/03; C08F 2500/08; C08F 2500/12
See application file for complete search history.

(56) References Cited

U.S. PATENT DOCUMENTS

| 5,064,802 | A | 11/1991 | Stevens et al. |
| 5,539,076 | A | 7/1996 | Nowlin et al. |
| 6,548,686 | B2 | 4/2003 | Nabika et al. |
| 2003/0171501 | A1 | 9/2003 | Kallio et al. |
| 2005/0054791 | A1 | 3/2005 | Nowlin et al. |
| 2007/0093603 | A1 | 4/2007 | Wooster et al. |
| 2007/0225158 | A1 | 9/2007 | Lee et al. |
| 2008/0255329 | A1 | 10/2008 | Boone et al. |
| 2010/0062927 | A1 | 3/2010 | Lee et al. |
| 2010/0087609 | A1 | 4/2010 | Park et al. |
| 2010/0121006 | A1 | 5/2010 | Cho et al. |
| 2011/0152529 | A1 | 6/2011 | Lee et al. |
| 2011/0160413 | A1 | 6/2011 | Lee et al. |
| 2011/0172451 | A1 | 7/2011 | Lee et al. |
| 2011/0177935 | A1 | 7/2011 | Lee et al. |
| 2012/0116035 | A1 | 5/2012 | Boone et al. |
| 2013/0203949 | A1 | 8/2013 | Lee et al. |
| 2013/0211020 | A1 | 8/2013 | Lee et al. |
| 2013/0211021 | A1 | 8/2013 | Lee et al. |
| 2013/0211023 | A1 | 8/2013 | Lee |
| 2013/0211024 | A1 | 8/2013 | Lee et al. |
| 2013/0296497 | A1 | 11/2013 | Jeong et al. |
| 2014/0066585 | A1 | 3/2014 | Boone et al. |
| 2015/0011770 | A1 | 1/2015 | Lee et al. |
| 2016/0046735 | A1* | 2/2016 | Lee et al. .................. C07F 7/28 526/160 |

FOREIGN PATENT DOCUMENTS

| EP | 2 559 695 A2 | 2/2013 |
| JP | 2010-514836 A | 5/2010 |
| JP | 2010-526203 A | 7/2010 |
| KR | 10-2001-0020425 A | 3/2001 |
| KR | 10-2005-0035183 A | 4/2005 |
| KR | 10-0820542 B1 | 4/2008 |
| KR | 10-2008-0058429 A | 8/2008 |
| KR | 10-2008-0101542 A | 11/2008 |
| KR | 10-0964093 B1 | 6/2010 |
| KR | 10-2010-0083076 A | 7/2010 |
| KR | 10-0986301 B1 | 10/2010 |
| KR | 10-1175338 B1 | 8/2012 |
| WO | WO 02/02323 A1 | 1/2002 |
| WO | WO 2004/111123 A1 | 12/2004 |

OTHER PUBLICATIONS

Chen et al., "A Novel Phenolate "Constrained Geometry" Catalyst System, Efficient Synthesis, Structural Characterization, and α-Olefin Polymerization Catalysis", Organometallics, vol. 16, No. 26, 1997, pp. 5958-5963.
Christie et al., Novel Routes to Bidentate Cyclopentadienyl-Alkoxide Complexes of Titanium: Synthesis of ($\eta^5$-σ-$C_5R^1_4CHR^2CH_2CR^3R^4O$)$TiCl_2$, Organometallics, vol. 18, No. 3, 1999, pp. 348-359.
Gibson et al., "Advances in Non-Metallocene Olefin Polymerization Catalysis", Chemical Reviews, vol. 103, No. 1, 2003, pp. 283-315.
Gielens et al., "Titanium Hydrocarbyl Complexes with a Linked Cyclopentadienyl-Alkoxide Ancillary Ligand; Participation of the Ligand in an Unusual Activation of a (Trimethylsilyl)methyl Group", Organometallics, vol. 17, No. 9, 1998, pp. 1652-1654.
Kim et al., "Preparation of Thiophene-Fused and Tetrahydroquinoline-Linked Cyclopentadienyl Titanium Complexes for Ethylene/α-Olefin Copolymerization", Catalysts, vol. 3, 2013, pp. 104-124.

(Continued)

*Primary Examiner* — Nathan M Nutter
(74) *Attorney, Agent, or Firm* — Birch, Stewart, Kolasch & Birch, LLP

(57) ABSTRACT

The present invention relates to an olefin-based polymer including an elution temperature 1 (Te1) and an elution temperature 2 (Te2), which are elution temperatures of the olefin-based polymer in a temperature range from −20° C. to 130° C. when measuring temperature rising elution fractionation (TREF) and having branch gradient number (BGN) from −1.0 to −0.001 when measuring chromatography Fourier transform infrared spectroscopy (GPC FT-IR).

17 Claims, 5 Drawing Sheets

(56) References Cited

OTHER PUBLICATIONS

Rau et al., "Synthesis and application in high-pressure polymerization of a titanium complex with a linked cytopentadienyl-phenoxide ligand", Journal of Organometallic Chemistry, vol. 608, 2000, pp. 71-75.

Turner et al., "Facile resolution of constrained geometry indenyl-phenoxide ligation", CHEM. COMMUN., 2003, pp. 1034-1035.

Zhang et al., "Constrained Geometry Tetramethylcyclopentadienyl-phenoxytitanium Dichlorides: Template Synthesis, Structures, and Catalytic Properties for Ethylene Polymerization", Organometallics, vol. 23, No. 3, 2004, pp. 540-546.

Extended European Search Report for Appl. No. 14847117.0 dated Jul. 12, 2016.

* cited by examiner

OLEFIN-BASED POLYMER

TECHNICAL FIELD

The present invention relates to an olefin-based polymer, and more particularly, to an olefin-based polymer including two elution temperatures of an elution temperature 1 (Te1) and an elution temperature 2 (Te2) in a specific temperature range when measuring temperature rising elution fractionation (TREF) and having a branch gradient number (BGN) in a specific range when measuring GPC FT-IR.

BACKGROUND ART

[Me$_2$Si(Me$_4$C$_5$)NtBu]TiCl$_2$ (Constrained-Geometry Catalyst, hereinafter, will be abbreviated as CGC) was reported by Dow Co. in the early 1990s (U.S. Pat. No. 5,064,802), and excellent aspects of the CGC in the copolymerization reaction of ethylene and alpha-olefin may be summarized in the following two points when compared to commonly known metallocene catalysts.

(1) At a high polymerization temperature, high activity is shown and a polymer having high molecular weight is produced, and (2) the copolymerization degree of alpha-olefin having large steric hindrance such as 1-hexene and 1-octene is excellent.

Meanwhile, a copolymer prepared by using the CGC catalyst includes a small amount of a low molecular weight part and may have improved physical properties such as strength, etc. when compared to a copolymer prepared by using a common Zeigler-Natta catalyst.

However, despite the above-described merits, the copolymer prepared by using the CGC catalyst has the defects of deteriorating processability when compared to the polymer prepared by using the common Zeigler-Natta catalyst.

U.S. Pat. No. 5,539,076 discloses a metallocene/non-metallocene blend catalyst system for preparing a specific bimodal copolymer having high density. The catalyst system is supported by an inorganic support. A supported Zeigler-Natta catalyst and a metallocene catalyst system has a drawback that a supported hybrid catalyst has lower activity than a homogeneous single catalyst, and the preparation of an olefin-based polymer having appropriate properties according to use is difficult. In addition, since the olefin-based polymer is prepared in a single reactor, gel that may be generated during the performing of a blending method may be produced, the insertion of a comonomer in a high molecular weight part may be difficult, the shape of a produced polymer may be poor, two polymer components may not be mixed homogeneously, and the control of quality may be difficult.

Thus, the development of an olefin-based polymer that may overcome the drawbacks of a common olefin-based polymer and provide improved physical properties is still required.

PRIOR ART DOCUMENTS

Patent Documents

U.S. Pat. No. 5,064,802
U.S. Pat. No. 6,548,686

Non-Patent Documents

Chem. Rev. 2003, 103, 283
Organometallics 1997, 16, 5958
Organometallics 2004, 23, 540
Chem. Commun. 2003, 1034
Organometallics 1999, 18, 348
Organometallics 1998, 17, 1652
J. Organomet. Chem. 2000, 608, 71

DISCLOSURE OF THE INVENTION

Technical Problem

There is provided an olefin-based polymer having a narrow molecular weight distribution, including an elution temperature 1 (Te1) and an elution temperature 2 (Te2) when measuring temperature rising elution fractionation (TREF) and having a branch gradient number (BGN) from −1.0 to −0.001.

Technical Solution

According to an aspect, there is provided an olefin-based polymer including an elution temperature 1 (Te1) and an elution temperature 2 (Te2), which are elution temperatures of the olefin-based polymer in a temperature range from −20° C. to 130° C. when measuring temperature rising elution fractionation (TREF) and having a branch gradient number (BGN) from −1.0 to −0.001 when measuring chromatography Fourier transform infrared spectroscopy (GPC FT-IR).

Advantageous Effects

The olefin-based polymer has a narrow molecular weight distribution, includes two of an elution temperature 1 (Te1) and an elution temperature 2 (Te2) when measuring temperature rising elution fractionation (TREF), and has branch gradient number (BGN) corresponding to a value from −1.0 to −0.001 when measuring chromatography Fourier transform infrared spectroscopy (GPC FT-IR).

The olefin-based polymer satisfying the above physical properties shows excellent tensile strength and elongation and may be used in diverse fields and uses including wrapping, construction, daily supplies, etc. such as a material of an automobile, a wire, a toy, a fiber, a medicine, etc.

BEST MODE FOR CARRYING OUT THE INVENTION

Figure 1:
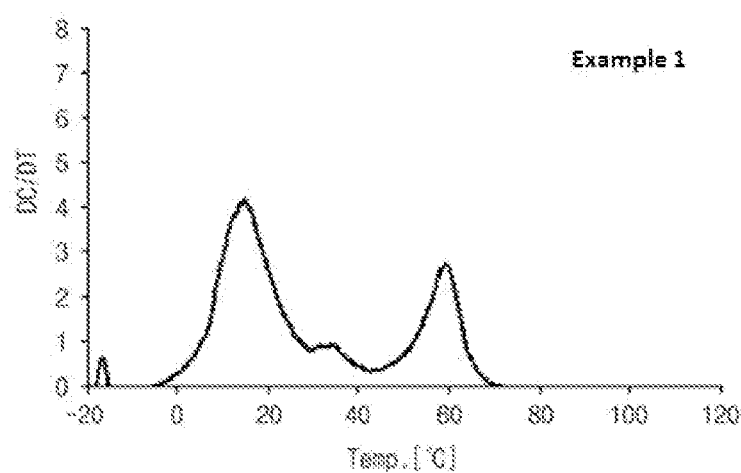
FIG. 1 illustrates a TREF graph of an olefin-based polymer prepared in Example 1.

Hereinafter, the present invention will be described in more detail to assist in the understanding of the present invention.

It will be understood that terms or words used in the specification and claims, should not be interpreted as having a meaning that is defined in dictionaries, but should be interpreted as having a meaning that is consistent with their meaning in the context of the present invention on the basis of the principle that the concept of the terms may be appropriately defined by the inventors for the best explanation of the invention.

To accomplish the technical tasks, there is provided an olefin-based polymer including an elution temperature 1 (Te1) and an elution temperature 2 (Te2), which are elution temperatures of the olefin-based polymer in a temperature range from −20° C. to 130° C. when measuring temperature rising elution fractionation (TREF) and having branch gradient number (BGN) from −1.0 to −0.001 when measuring chromatography Fourier transform infrared spectroscopy (GPC FT-IR).

In the specification, the term "a polymer" denotes a polymer compound prepared by the polymerization of monomers having the same or different types. The general term "the polymer" includes "a hybrid polymer" as well as "a homopolymer," "a copolymer" and "a tercopolymer."

"The hybrid polymer" denotes a polymer prepared by the polymerization of at least two different types of monomers. The general term "the hybrid polymer" denotes "the copolymer" (commonly used for denoting a polymer prepared using two different types of monomers) and "the tercopolymer" (commonly used for denoting a polymer prepared using three different types of monomers). "The hybrid polymer" includes a polymer prepared by the polymerization of at least four different types of monomers.

In the specification, the term "semicrystalline" designates a polymer having a first transition temperature measured by TREF, differential scanning calorimetry (DSC), or other equivalent technique, a crystalline melting temperature (Tm), an elution point, etc. The density, the Tm, the elution point, etc. of the semicrystal may be dependent on the crystallinity thereof. The term "amorphous" designates a polymer having no crystalline melting temperature when measured by TREF, DSC, or other equivalent technique.

The olefin-based polymer according to the specification may have narrow molecular weight distribution, include two of Te1 and Te2 in a specific temperature range when measuring TREF and have BGN from −1.0 to −0.001 when measuring GPC FT-IR. The olefin-based polymer satisfying the above physical properties has excellent tensile strength and elongation and may be used in diverse fields and uses including wrapping, construction, daily supplies, etc. such as a material of an automobile, a wire, a toy, a fiber, a medicine, etc.

In general, when a blend catalyst of at least two is used, two Te peaks of TREF may be present. However, in this case, the activity and copolymerization degree of each in the bend catalyst are difficult to expect and control, and the preparation of an olefin-based polymer having appropriate properties according to use may be difficult. In addition, at least two catalyst components may not be mixed homogeneously, and the control of quality may become difficult.

In addition, when two Te are shown when measuring TREF, it would be generally expected that at least two polymers including different branch amounts of polymers are blended. In this case, a BGN constant may be changed according to branch amount distribution in a polymer, and the strength and physical properties of a base resin and a compound product may be changed.

In addition, molecular weight distribution may increase in general after blending at least two kinds of polymers. In this case, impact strength and mechanical properties may decrease, and the blocking phenomenon may be generated.

Therefore, the olefin-based polymer in the specification may include two of Te1 and Te2 when measuring TREF and have BGN from −0.1 to −0.001. In addition, an olefin-based polymer having narrow molecular weight distribution may be provided.

The olefin-based polymer according to the specification may include a first semicrystalline olefin-based polymer and a second semicrystalline olefin-based polymer and have a peak for the first semicrystalline olefin-based polymer (P1) and a peak for the second semicrystalline olefin-based polymer (P2) in a temperature range from −20° C. to 130° C. Te of each peak may be expressed by Te1 and Te2, respectively.

The olefin-based polymer according to an embodiment may further include at least one peak including an amorphous peak in a minimum temperature (extremely low temperature) range from −20° C. to −10° C. other than the two semicrystalline peaks. A common olefin-based polymer has one semicrystalline peak; however the olefin-based polymer according to an embodiment of the specification may have two semicrystalline peaks, thereby increasing mechanical properties, etc.

The measuring of the TREF in the specification may be conducted by using, for example, a TREF apparatus of PolymerChar Co. and using an o-dichlorobenzene solvent while elevating the temperature from −20° C. to 130° C.

When measuring TREF with respect to the olefin-based polymer according to an embodiment, the Te1 may be present at a relatively lower temperature than the Te2. When the density of the olefin-based polymer is in a range from 0.85/cc to 0.91 g/cc, Te1 may be in a range from −20° C. to 100° C., and Te2 may be in a range from 0° C. to 130° C.

The Te used in the specification means the temperature at the highest point of each peak in a TREF elution graph expressed by an elution amount with respect to temperature (dC/dT), and a fraction ratio may be calculated as an integration value of a temperature-elution amount graph.

Particularly, according to another embodiment, when measuring TREF when the density of the olefin-based polymer is in a range from 0.85 g/cc to 0.87 g/cc, the Te1 may be in a range from −20° C. to 30° C., and the Te2 may be in a range from 30° C. to 80° C.

According to a further another embodiment, when measuring TREF when the density of the olefin-based polymer is in a range from 0.87 g/cc to 0.89 g/cc, the Te1 may be in a range from 0° C. to 50° C., and the Te2 may be in a range from 50° C. to 100° C.

According to a still further another embodiment, when measuring TREF when the density of the olefin-based polymer is in a range from 0.89 g/cc to 0.91 g/cc, the Te1 may be in a range from 20° C. to 70° C., and the Te2 may be in a range from 70° C. to 130° C.

According to an even further another embodiment, when measuring TREF, the fraction ratio of the peak for the first semicrystalline olefin-based polymer (P1) may be from 5 to 95%, may particularly be from 10 to 90%, and may more particularly be from 20 to 90%. In addition, the fraction ratio of the peak for the second semicrystalline olefin-based polymer (P2) may be from 5 to 95%, may particularly be from 10 to 90%, and may more particularly be from 10 to 80%.

In addition, for the calculation of the fraction ratio, the initiation point of each peak in the graph of an elution amount with respect to the temperature (dC/dT) is defined as a point initiating the elution of the polymer on the basis of a base line, and the end point of each peak is defined as a point terminating the elution of the polymer on the basis of the base line.

In the case that the peak for the first semicrystalline olefin-based polymer (P1) and the peak for the second semicrystalline olefin-based polymer (P2) may be partially overlapped, a point where an elution amount value (dC/dT) may be the lowest in an overlapped area may be defined as the terminal point of the P1 peak and as the initiation point of the P2 peak.

In addition, a peak exhibited at a temperature range from −20° C. to −10° C. may be shown by the blending of an amorphous polymer and a low crystalline polymer, and the peak exhibited at this position may be treated by adding to the fraction ratio of the P1 peak.

In addition, the olefin-based polymer according to an embodiment may include Tm1 and Tm2, which are melting temperatures Tm obtained in a DSC graph. In the density range of the olefin-based polymer from 0.85 to 0.91 g/cc, the Tm1 may be in a range from −30 to 120° C., and the Tm2 may be in a range from −10 to 140° C.

When a polymer is prepared using a common metallocene catalyst, one Tm is present. However, when two Tms are present, crystal may be melted and crystallized at different temperatures, and thermal stability and mechanical strength may increase.

In addition, when a blend catalyst of at least two is used, two Tms may be present. However, in this case, the activity and copolymerization degree of each in the blend catalyst are difficult to expect and control, and the preparation of an olefin-based polymer having appropriate properties according to use may become difficult. In addition, since the blending of at least two catalyst components may be inhomogeneous, the control of quality may be difficult.

The Tm used in the specification means the highest point of each peak in the temperature-heat flow graph of DSC.

According to an embodiment, when the density is from 0.85 g/cc to 0.87 g/cc, the Tm1 may be in a range from −30° C. to 45° C., and the Tm2 may be in a range from 45° C. to 110° C.

In addition, according to another embodiment, when the density is from 0.87 g/cc to 0.89 g/cc, the Tm1 may be in a range from 20° C. to 75° C., and the Tm2 may be in a range from 75° C. to 120° C.

In addition, according to a further embodiment, when the density is from 0.89 g/cc to 0.91 g/cc, the Tm1 may be in a range from 30° C. to 90° C., and the Tm2 may be in a range from 90° C. to 140° C.

Meanwhile, the BGN of the olefin-based polymer according to an embodiment may be from −1.0 to −0.001. Particularly, the BGN of the olefin-based polymer may be in a range from −0.8 to −0.001, may preferably be from −0.5 to −0.001 and may most preferably be −0.3 to −0.001.

According to the BGN of the olefin-based polymer, the strength and the physical properties of a base resin and a compound product may be changed. When the BGN has the above-described range, the physical properties of the base resin such as the tensile strength and the elongation may increase.

The term "BGN" used in the specification is the measure showing the distribution shape of a comonomer such as alpha-olefin according to molecular weight and may be defined by the following Equation 1.

[Equation 1]

$$\text{Branch Gradient Number}(BGN) = \frac{(\text{Branch amount of high molecular weight} - \text{Branch amount of low molecular weight})}{(\text{Branch amount of low molecular weight})}$$

In the above Equation 1,

The low molecular weight means the molecular weight in the bottom 10%, and the high molecular weight means the molecular weight in the top 10% of total molecular weight distribution, and the branch amount means the amount of a branch having at least two carbon atoms per 1,000 carbon atoms.

The branch in the BGN means a branch attached to a main chain induced from and obtained by using alpha-olefins such as propylene, 1-butene, 1-hexene, 1-octene, etc. as a comonomer.

In addition, the branch may include both a short carbon branch (SCB) having 2 to 6 carbon atoms and a long carbon branch (LCB) having at least 7 carbon atoms.

When the BGN is a positive (+) value, the branch amount in a low molecular weight region is small, and the branch amount in a high molecular weight region is relatively large. On the contrary, when the BGN value is a negative (−) value, the branch amount in a low molecular weight region is large, and the branch amount in a high molecular weight region is relatively small.

In general, if two peaks are present when measuring TREF, at least two kinds of polymers having different branch amounts are blended. In this case, a BGN constant may be changed according to branch amount distribution in the polymer, and the strength and the physical properties of a base resin and a compound product may be changed. In addition, molecular weight distribution may increase when blending at least two kinds of polymers in general, and in this case, impact strength and mechanical properties may decrease, and the blocking phenomenon may occur.

According to the specification, a polymer having two peaks Te1 and Te2 when measuring TREF, BGN from −1.0 to −0.001, and narrow molecular weight distribution may be provided. The olefin-based polymer having the physical properties may have improved mechanical properties such as tensile strength and elongation.

According to the specification, the molecular weight, the molecular weight distribution and the branch amount may be measured continuously and simultaneously by using a GPC-FTIR apparatus or a cross-fractionation chromatography (CFC) apparatus, and the BGN value may be obtained from the data thereof.

Meanwhile, the olefin-based polymer according to an embodiment has melting index (MI) when measured under the conditions of 190° C. and 2.16 kg weight according to ASTM D1238, from about 0.1 to about 2,000 g/10 min, preferably from about 0.1 to about 1,000 g/10 min, and more preferably from about 0.1 to 500 g/10 min, without limitation.

The weight average molecular weight of the olefin-based polymer may be from about 10,000 to about 500,000 g/mol and may preferably be from about 20,000 to about 200,000 g/mol, without limitation.

According to an embodiment, the molecular weight distribution (MWD) of the olefin-based polymer may be from about 1.0 to about 3.0, may preferably be from about 1.5 to 3.0, and may more preferably be from 2.5 to 2.8.

The olefin-based polymer having the above-described physical properties according to an embodiment may be prepared by polymerizing an olefin-based monomer using a catalyst composition including a transition metal compound of the following Formula 1.

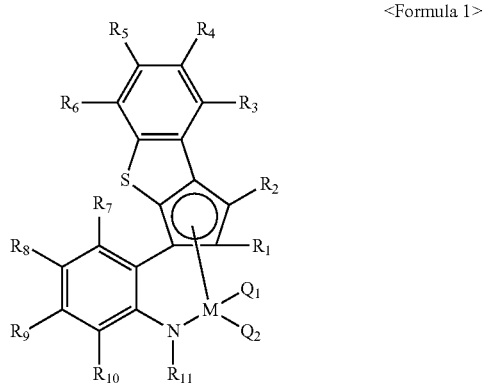

<Formula 1>

In the above Formula 1,

M is a transition metal in group 4, $Q_1$ and $Q_2$ may be the same or different and independently hydrogen; halogen; alkyl having 1 to 20 carbon atoms; alkenyl having 2 to 20 carbon atoms; aryl having 6 to 20 carbon atoms; alkylaryl having 6 to 20 carbon atoms; arylalkyl having 7 to 20 carbon atoms; alkyl amido having 1 to 20 carbon atoms; aryl amido having 6 to 20 carbon atoms; or alkylidene having 1 to 20 carbon atoms, $R_1$ to $R_6$ may be the same or different and independently hydrogen; silyl; alkyl having 1 to 20 carbon atoms; alkenyl having 2 to 20 carbon atoms; aryl having 6 to 20 carbon atoms; alkylaryl having 7 to 20 carbon atoms; arylalkyl having 7 to 20 carbon atoms; or a metalloid radical of a metal in group 14 substituted with hydrocarbyl having 1 to 20 carbon atoms; $R_1$ and $R_2$ may be connected from each other, or at least two of $R_3$ to $R_6$ may be connected to each other to form an aliphatic ring having 5 to 20 carbon atoms or an aromatic ring having 6 to 20 carbon atoms; the aliphatic ring or the aromatic ring may be substituted with halogen, alkyl having 1 to 20 carbon atoms, alkenyl having 2 to 20 carbon atoms or aryl having 6 to 20 carbon atoms, and $R_7$ to $R_{11}$ may be the same or different and independently hydrogen; alkyl having 1 to 20 carbon atoms; alkenyl having 2 to 20 carbon atoms; aryl having 6 to 20 carbon atoms; alkylaryl having 7 to 20 carbon atoms; or arylalkyl having 7 to 20 carbon atoms; at least two adjacent to each other of $R_7$ to $R_{11}$ may be connected to each other to form an aliphatic ring having 5 to 20 carbon atoms or an aromatic ring having 6 to 20 carbon atoms; the aliphatic ring or the aromatic ring may be substituted with halogen, alkyl having 1 to 20 carbon atoms, alkenyl having 2 to 20 carbon atoms or aryl having 6 to 20 carbon atoms.

$R_1$ to $R_{11}$ may be independently unsubstituted or substituted, and for the substituted $R_1$ to $R_{11}$, a substituent may be halogen, alkyl having 1 to 20 carbon atoms, hydrocarbyl having 1 to 20 carbon atoms, alkoxy having 1 to 20 carbon atoms or aryloxy having 6 to 20 carbon atoms.

In the transition metal compound of the above Formula 1 described in the specification, a metal site is connected to a cyclopentadienyl ligand connected to a phenylene bridge introducing an amido group, and the structure thereof has a narrow Cp-M-N angle and a wide $Q_1$-M-$Q_2$ angle to which a monomer may approach. In addition, different from a CGC structure connected by a silicon bridge, the sites of cyclopentadiene fused with benzothiophene via the bonding of a ring shape, the phenylene bridge, nitrogen and the metal may be connected in order to form a stable and rigid pentagonal ring structure in the compound structure represented by the above Formula 1.

Thus, when applying these compounds for the polymerization of olefin after reacting with a promotor such as methyl aluminoxane or $B(C_6F_5)_3$ and activating, polyolefin having high activity, high molecular weight and high copolymerization degree may be produced even at a high polymerization temperature. Particularly, since a large amount of alpha-olefin may be introduced as well as linear polyethylene having low density of 0.910-0.930 g/cc due to the structural characteristics of the catalyst, a polyolefin copolymer having extremely low density of less than 0.910 g/cc may be produced.

In particular, a polymer having narrow MWD, good copolymerization degree and high molecular weight in a low density region may be prepared by using a catalyst composition including the transition metal compound.

In addition, diverse substituents may be introduced in a cyclopentadienyl group fused with benzothiophene and quinolines, and electronic and steric environment around a metal may be easily controlled, and so, the structure and physical properties of the polyolefin thus produced may be controlled. The compound of the above Formula 1 may be preferably used for preparing a catalyst for polymerizing an olefin-based monomer, however the present invention is not limited thereto. The transition metal compound may be used in any other applicable fields.

In the specification, alkyl and alkenyl may be a linear or branched alkyl or alkenyl.

In the specification, silyl may be a substituted silyl with alkyl having 1 to 20 carbon atoms, for example, trimethylsilyl or triethylsilyl.

In the specification, aryl may include a single ring aryl or a polyring aryl, for example, phenyl, naphthyl, anthryl, phenanthryl, crysenyl, pyrenyl, etc.

According to an embodiment, $R_1$ and $R_2$ may be alkyl having 1 to 20 carbon atoms.

According to another embodiment, $R_1$ and $R_2$ may be alkyl having 1 to 6 carbon atoms.

According to another embodiment, $R_1$ and $R_2$ may be methyl.

According to another embodiment, $R_3$ to $R_6$ may be the same or different, and independently hydrogen; alkyl having 1 to 20 carbon atoms; or alkenyl having 2 to 20 carbon atoms.

According to another embodiment, $R_3$ to $R_6$ may be the same or different and independently hydrogen; or alkyl having 1 to 20 carbon atoms.

According to another embodiment, $R_3$ to $R_6$ may be the same or different and independently hydrogen.

According to another embodiment, M may be Ti, Hf or Zr.

According to another embodiment, $R_{11}$ may be connected to adjacent $R_{10}$ from each other to form an aliphatic ring having 5 to 20 carbon atoms or an aromatic ring having 6 to carbon atoms. In addition, the aliphatic ring or the aromatic ring may be substituted with halogen, alkyl having 1 to 20 carbon atoms, alkenyl having 2 to 20 carbon atoms or aryl having 6 to 20 carbon atoms.

According to another embodiment, $R_{11}$ may be unsubstituted or substituted alkyl having 1 to 20 carbon atoms, aryl having 6 to 20 carbon atoms or alkylaryl having 7 to 20 carbon atoms.

In this case, a substituent may be halogen, alkyl having 1 to 20 carbon atoms, hydrocarbyl having 1 to 20 carbon atoms, alkoxy having 1 to 20 carbon atoms or aryloxy having 6 to 20 carbon atoms.

According to another embodiment, $R_7$ to $R_{10}$ may be hydrogen.

According to another embodiment, when $R_{11}$ is the unsubstituted or substituted alkyl having 1 to 20 carbon atoms, aryl having 6 to 20 carbon atoms or alkylaryl having 7 to 20 carbon atoms, the compound represented by the above Formula 1 may be, for example, one or at least two transition metal compounds selected from the group consisting of the compounds represented by the following Formulae.

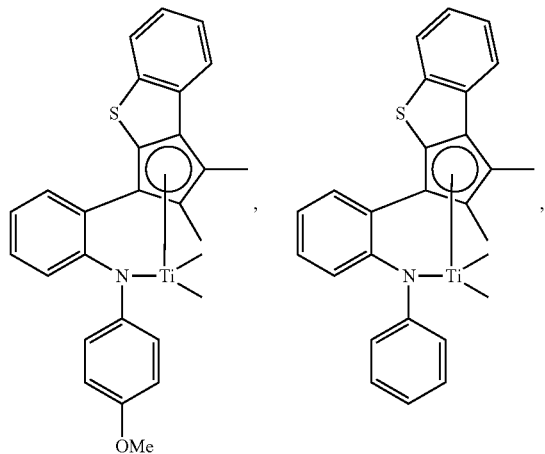

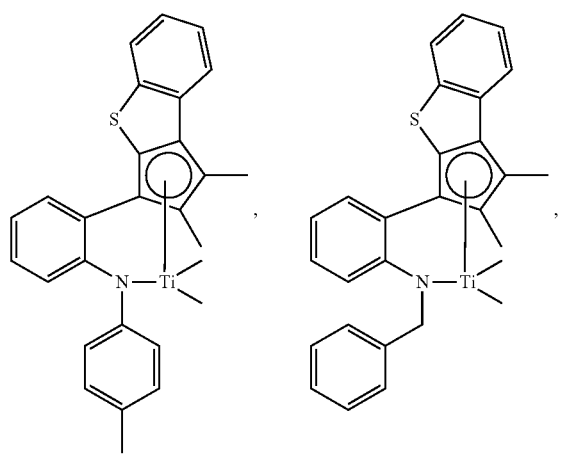

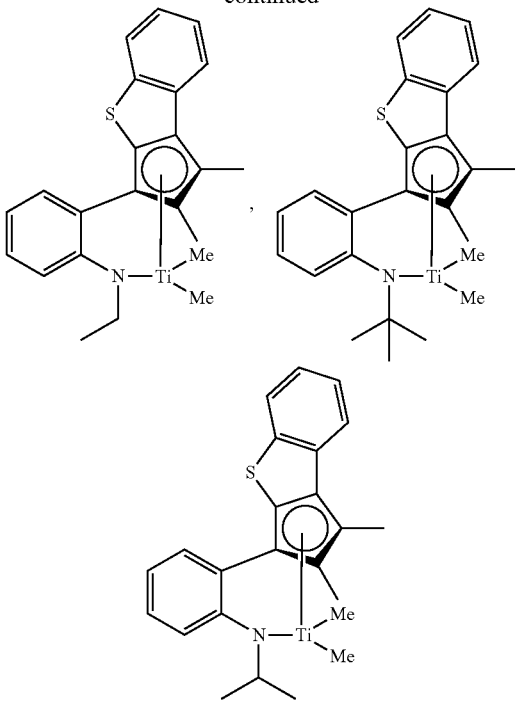

According to another embodiment, in the case that $R_{11}$ may be connected to $R_{10}$ adjacent to $R_{11}$ from each other to form an aliphatic ring having 5 to 20 carbon atoms or an aromatic ring having 6 to 20 carbon atoms, the compound represented by the above Formula 1 may be represented by the following Formula 2.

<Formula 2>

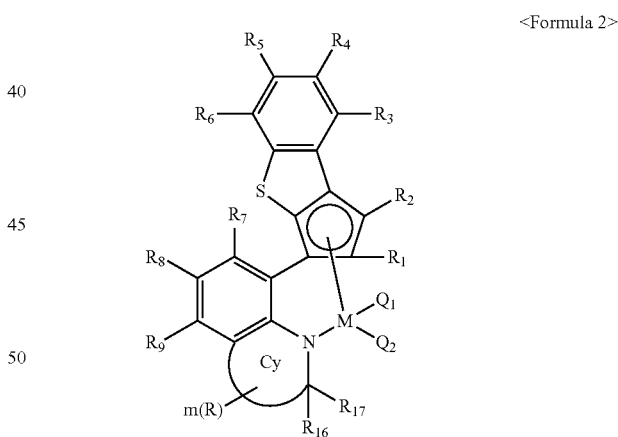

In the above Formula 2,

M, $Q_1$, $Q_2$, and $R_1$ to $R_9$ are the same as defined in the above Formula 1, Cy may be a five-membered or six-membered aliphatic ring, R, $R_{16}$ and $R_{17}$ may be independently hydrogen; alkyl having 1 to 20 carbon atoms; alkenyl having 2 to 20 carbon atoms; aryl having 6 to 20 carbon atoms; alkylaryl having 7 to 20 carbon atoms; or arylalkyl having 7 to 20 carbon atoms;

in the case when Cy is the five-membered aliphatic ring, m is an integer from 0 to 2, and in the case when Cy is the six-membered aliphatic ring, m is an integer from 0 to 4.

According to an embodiment, the above Formula 2 may be represented by the following Formula 2-1 or 2-2.

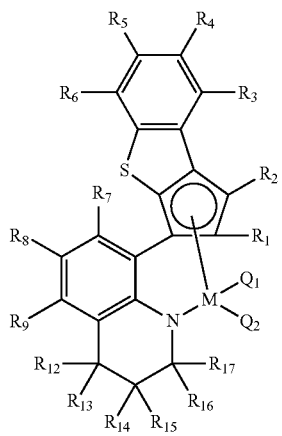
<Formula 2-1>

In the above Formula 2-1, $R_{12}$ to $R_{17}$ may be independently hydrogen; alkyl having 1 to 20 carbon atoms; alkenyl having 2 to 20 carbon atoms; aryl having 6 to 20 carbon atoms; alkylaryl having 7 to 20 carbon atoms; or arylalkyl having 7 to 20 carbon atoms, and the remaining substituents are the same as defined in Formula 1.

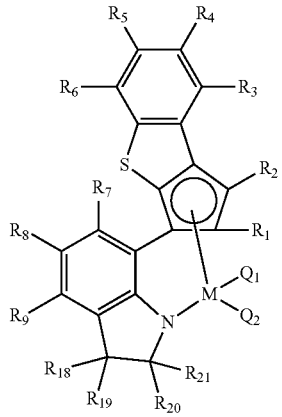
<Formula 2-2>

In the above Formula 2-2, $R_{18}$ to $R_{21}$ may be independently hydrogen; alkyl having 1 to 20 carbon atoms; alkenyl having 2 to 20 carbon atoms; aryl having 6 to 20 carbon atoms; alkylaryl having 7 to 20 carbon atoms; or arylalkyl having 7 to 20 carbon atoms, and the remaining substituents are the same as defined in Formula 1.

The compound of the above Formula 1 may be prepared by the following steps:

a) preparing a compound represented by the following <Formula 6> by reacting an amine compound represented by the following <Formula 5> with an alkyllithium, and adding a compound including a protecting group (—$R_0$);

b) preparing an amine compound represented by the following <Formula 8> by reacting a compound represented by the above <Formula 6> with an alkyllithium, and adding a ketone compound represented by the following <Formula 7>;

c) preparing a dilithium compound represented by the following <Formula 9> by reacting a compound represented by the above <Formula 8> with n-butyllithium; and d) preparing a transition metal compound represented by Formula 1 by reacting a compound represented by the above <Formula 9>, $MCl_4$ (M=a transition metal in group 4), and an organolithium.

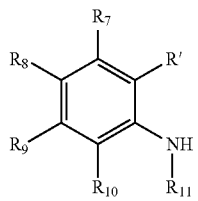
<Formula 5>

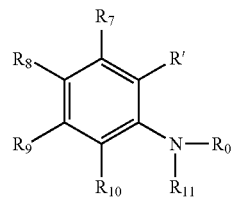
<Formula 6>

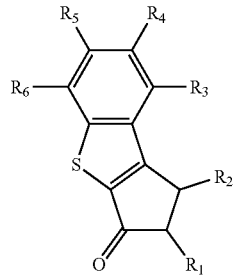
<Formula 7>

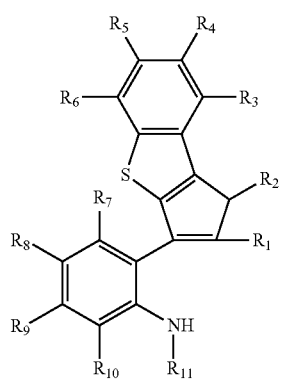
<Formula 8>

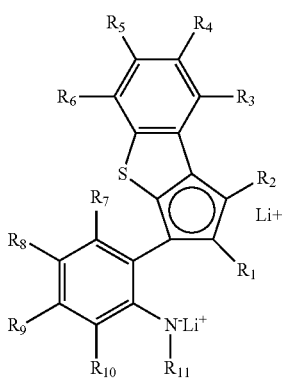

<Formula 9>

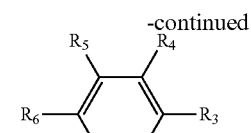

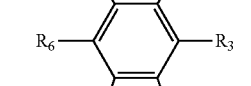

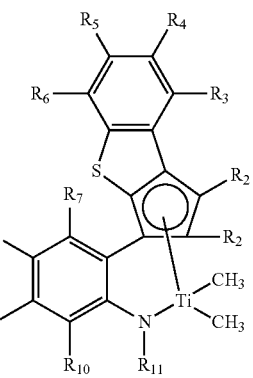

In the above Formulae 5 to 9,

R' may be hydrogen,

R₀ may be a protecting group, and other substituents are the same as defined in Formula 1.

In the above step a), a compound including the protecting group may be selected from trimethylsilyl chloride, benzyl chloride, t-butoxycarbonyl chloride, benzyloxycarbonyl chloride and carbon dioxide.

When the compound including the protecting group is the carbon dioxide, the above Formula 6 may be a lithium carbamate compound represented by the following Formula 6a.

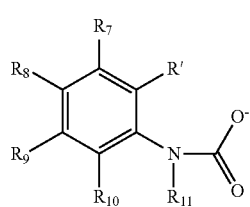

<Formula 6a>

The substituents are the same as defined in Formula 1.

According to a particular embodiment, the compound of Formula 1 may be prepared by the following Reaction 1.

<Reaction 1>

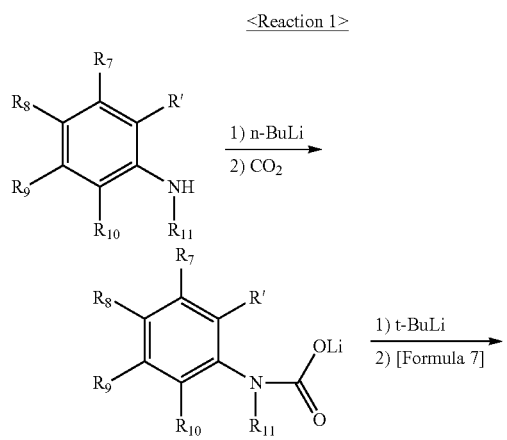

In the above Reaction 1, substituents are the same as defined in Formula 1.

The specification may also provide a catalyst composition including the compound of the above Formula 1.

The catalyst composition may further include a promotor. Known materials in this field may be used as the promotor.

For example, the catalyst composition may further include at least one of the following Formulae 12 to 14 as the promotor.

—[Al(R₁₈)—O]a-                <Formula 12>

In the above Formula, $R_{18}$ may be independently a halogen radical; a hydrocarbyl radical having 1 to 20 carbon atoms; or a hydrocarbyl radical having 1 to 20 carbon atoms substituted with halogen, and a is an integer greater than or equal to 2.

D(R₁₈)₃                <Formula 13>

In the above Formula, D may be aluminum or boron, and $R_{16}$ is the same as in the above Formula 12.

[L-H]+[Z(A)₄]- or [L]+[Z(A)₄]-                <Formula 14>

In the above Formula, L may be a neutral or cationic Lewis acid, H may be a hydrogen atom, Z may be an element in group 13, and A may be independently aryl having 6 to 20 carbon atoms or alkyl having 1 to 20 carbon atoms, where hydrogen atom may be substituted with a substituent, and the substituent may be halogen, hydrocarbyl having 1 to 20 carbon atoms, alkoxy having 1 to 20 carbon atoms, or aryloxy having 6 to 20 carbon atoms.

According to an embodiment, first, a method including a step of obtaining a mixture by contacting the catalyst composition with a compound represented by the above Formula 12 or Formula 13; and a step of adding a compound represented by the above Formula 14 into the mixture may be provided as the method of preparing the catalyst composition.

Second, a method of preparing a catalyst composition by contacting the catalyst composition with the compound represented by the above Formula 14 may be provided.

According to another embodiment, in the first method among the preparing methods of the catalyst composition according to the above embodiment, the molar ratio of the compound represented by the above Formula 12 or Formula 13 with respect to the catalyst composition may preferably be from 1:2 to 1:5,000, may more preferably be from 1:10 to 1:1,000, and may most preferably be from 1:20 to 1:500.

Meanwhile, the molar ratio of the compound represented by the above Formula 14 with respect to the catalyst composition may preferably be from 1:1 to 1:25, may more preferably be from 1:1 to 1:10, and may most preferably be from 1:1 to 1:5.

In the case that the molar ratio of the compound represented by the above Formula 12 or Formula 13 with respect to the catalyst composition is less than 1:2, the amount of an alkylating agent is very small, and the alkylation of a metal compound may not be completely carried out, and when the molar ratio exceeds 1:5,000, the activation of the alkylated metal compound may not be completely carried out due to the side reaction of the remaining excessive alkylating agent with the activation agent of the above Formula 14 even though the alkylation of the metal compound may be carried out.

In addition, in the case that the molar ratio of the compound represented by the above Formula 14 with respect to the transition metal compound of the above Formula 1 is less than 1:1, the amount of the activation agent is relatively small, and the activation of the metal compound may not be completely carried out, thereby deteriorating the activity of the catalyst composition prepared. In the case that the molar ratio exceeds 1:25, the remaining excessive amount of the activation agent may decrease the economic performance in consideration of the unit price of the catalyst composition, or the purity of a polymer thus produced may be decreased even though the activation of the metal compound may be completely carried out.

According to another embodiment, in the second method among the preparing methods of the catalyst composition according to the above embodiment, the molar ratio of the compound represented by the above Formula 14 with respect to the catalyst composition may preferably be from 1:1 to 1:500, may more preferably be from 1:1 to 1:50, and may most preferably be from 1:2 to 1:25. In the case that the molar ratio is less than 1:1, the amount of the activation agent is relatively small, and the activation of the metal compound may not be completely carried out, thereby deteriorating the activity of the catalyst composition prepared. In the case that the molar ratio exceeds 1:500, the remaining excessive amount of the activation agent may decrease the economic performance in consideration of the unit price of the catalyst composition, or the purity of a polymer thus produced may be decreased even though the activation of the metal compound may be completely carried out.

According to another embodiment, a reaction solvent including an aliphatic hydrocarbon solvent having 5 to 12 carbon atoms such as pentane, hexane, heptane, etc., a hydrocarbon solvent substituted with a chlorine atom such as dichloromethane and chlorobenzene, or an aromatic hydrocarbon solvent such as benzene, toluene, etc. may be used during the preparation of the catalyst composition. However, the solvent is not limited thereto, and all solvents useful in this field may be used. The solvent used is preferably treated with a small amount of alkylaluminum to remove a trace amount of water or air functioning as a catalytic poison, and a promotor may be further included.

In addition, the composition may further include an additive. For example, the composition may include a compound containing a hetero atom. Particularly, the compound containing a hetero atom may include a heterocyclic compound; or an alkane containing a hetero atom.

Examples of the heterocyclic compound may include an aromatic ring containing a hetero atom; a heterocycloalkane; or a heterocycloalkene.

Examples of the alkane containing a hetero atom may include an alkane including an amine group or an ether group.

The aromatic ring containing a hetero atom; the heterocycloalkane; or the heterocycloalkene may include a five membered or six membered ring.

The compound containing a hetero atom may include O, S, Se, N, P or Si as the hetero atom.

The compound containing a hetero atom may include one hetero atom.

The compound containing a hetero atom may be substituted, and in the case that the compound containing a hetero atom is substituted, the compound may be substituted with at least one selected from the group consisting of hydrogen, methyl, phenyl and benzyl.

Examples of the compound containing a hetero atom may include at least one selected from the group consisting of pyridine, 3,5-dimethylpyridine, 2,4,6-trimethylpyridine, 2,6-dimethylpyridine, 2,4-dimethylpyridine, thiophene, 2-methylthiophene, 2,3-dimethylthiophene, piperidine, phosphinine, pyrrole, 2-methylpyrrole, aniline, p-toluidine, tetrahydrofuran, 2,3-dimethyltetrahydrofuran, 2,5-tetrahydrofuran, 3,4-dihydro-2H-pyrene, furan, 2-methylfuran, 2,3-dimethylfuran, 2,5-dimethylfuran, diethyl ether, methyl t-butyl ether and triethylamine, without limitation.

In addition, the catalyst composition and the promotor may be used as a supported state on a support. As the support, silica-alumina, silica-magnesia, etc. may be used, and other optional support known in this art may be used. In addition, this support may be used as a dried state at a high temperature. The drying temperature may be, for example, from 180° C. to 800° C. In the case that the drying temperature is excessively low and less than 180° C., an excessive amount on the support may react with the promoter and deteriorate the performance. In the case that the drying temperature is excessively high and exceeds 800° C., the amount of a hydroxyl group on the surface of the support may decrease and decrease reaction site with the promotor.

According to another embodiment, the compound represented by the above Formula 12 may be any alkylaluminoxane, without specific limitation. Preferably, methylaluminoxane, ethylaluminoxane, isobutylaluminoxane, butylaluminoxane, etc. may be used, and methylaluminoxane may be particularly preferably used.

According to another embodiment, the compound represented by the above Formula 13 is not specifically limited and may include trimethylaluminum, triethylaluminum, triisobutylaluminum, tripropylaluminum, tributylaluminum, dimethylchloroaluminum, triisopropylaluminum, tri-s-butylaluminum, tricyclopentylaluminum, tripentylaluminum, triisopentylaluminum, trihexylaluminum, trioctylaluminum, ethyldimethylaluminum, methyldiethylaluminum, triphenylaluminum, tri-p-tolylaluminum, dimethylaluminummethoxide, dimethylaluminumethoxide, trimethylboron, triethylboron, triisobutylboron, tripropylboron, tributylboron, etc. Particularly, the compound may preferably be selected from trimethylaluminum, triethylaluminum and triisobutylaluminum.

According to another embodiment, the compound represented by the above Formula 14 is not specifically limited and may include triethylammoniumtetraphenylboron, tributylammoniumtetraphenylboron, trimethylammoniumtetraphenylboron, tripropylammoniumtetraphenylboron, trimethylammoniumtetra(p-tolyl)boron, trimethylammoniumtetra(o,p-dimethylphenyl)boron, tributylammoniumtetra(p-trifluoromethylphenyl)boron, trimethylammoniumtetra(p-trifluoromethylphenyl)boron, tributylammoniumtetrapentafluorophenylboron, N,N-diethylaniliniumtetraphenylboron, N,N-diethylaniliniumtetraphenylboron, N,N-diethylaniliniumtetrapentafluorophenylboron, diethylammoniumtetrapentafluorophenylboron, triphenylphosphoniumtetraphenylboron, trimethylphosphoniumtetraphenylboron, triethylammoniumtetraphenylaluminum, tributylammoniumtetraphenylaluminum, trimethylammoniumtetraphenylaluminum, tripropylammoniumtetraphenylaluminum, trimethylammoniumtetra(p-tolyl)aluminum, tripropylammoniumtetra(p-tolyl)aluminum, triethylammoniumtetra(o,p-dimethylphenyl)aluminum, tributylammoniumtetra(p-trifluoromethylphenyl)aluminum, trimethylammoniumtetra(p-trifluoromethylphenyl)aluminum, tributylammoniumtetrapentafluorophenylaluminum, N,N-diethylaniliniumtetraphenylaluminum, N,N-diethylaniliniumtetraphenylaluminum, N,N-diethylaniliniumtetrapentafluorophenylaluminum, diethylammoniumtetrapentatetraphenylaluminum, triphenylphosphoniumtetraphenylaluminum, trimethylphosphoniumtetraphenylaluminum, triethylammoniumtetraphenylaluminum, tributylammoniumtetraphenylaluminum, trimethylammoniumtetraphenylboron, tripropylammoniumtetraphenylboron, trimethylammoniumtetra(p-tolyl)boron,tripropylammoniumtetra(p-tolyl)boron, triethylammoniumtetra(o,p-dimethylphenyl)boron, trimethylammoniumtetra(o,p-dimethylphenyl)boron, tributylammoniumtetra(p-trifluoromethylphenyl)boron, trimethylammoniumtetra(p-trifluoromethylphenyl)boron, tributylammoniumtetrapentafluorophenylboron, N,N-diethylaniliniumtetraphenylboron, N,N-diethylaniliniumtetraphenylboron, N,N-diethylaniliniumtetrapentafluorophenylboron, diethylammoniumtetrapentafluorophenylboron, triphenylphosphoniumtetraphenylboron, triphenylcarboniumtetra(p-trifluoromethylphenyl)boron, triphenylcarboniumtetrapentafluorophenylboron, etc.

According to another embodiment, the olefin-based monomer may include an alpha-olefin-based monomer, a cyclic olefin-based monomer, a diene olefin-based monomer, a triene olefin-based monomer, a styrene-based monomer, etc., and may be obtained by homopolymerizing one kind thereof or by blending at least two thereof.

The alpha-olefin-based monomer includes an aliphatic olefin having 2 to 12 carbon atoms, and preferably 2 to 8 carbon atoms, and particularly includes ethylene, propylene, 1-butene, 1-pentene, 3-methyl-1-butene, 1-hexene, 4-methyl-1-pentene, 3-methyl-1-pentene, 1-heptene, 1-octene, 1-decene, 4,4-dimethyl-1-pentene, 4,4-diethyl-1-hexene, 3,4-dimethyl-1-hexene, etc. In addition, the alpha-olefin may be homopolymerized or alternating, random or block copolymerized. The copolymerization of the alpha-olefin include the copolymerization of ethylene with the alpha-olefin having 2 to 12 carbon atoms, preferably having 2 to 8 carbon atoms (ethylene with propylene, ethylene with 1-butene, ethylene with 1-hexene, ethylene with 4-methyl-1-pentene and ethylene with 1-octene) and the copolymerization of propylene with the alpha-olefin having 2 to 12 carbon atoms, preferably having 2 to 8 carbon atoms (propylene with 1-butene, propylene with 4-methyl-1-pentene, propylene with 4-methyl-1-butene, propylene with 1-hexene and propylene with 1-octene).

In the copolymerization of the ethylene or propylene with other alpha-olefin, the amount of the other alpha-olefin may be selected from less than or equal to 90 wt % based on the total amount of the monomer. In general, the amount of the other alpha-olefin may be less than or equal to 70 wt %, preferably less than or equal to 60 wt %, and more preferably less than or equal to 50 wt % for an ethylene copolymer, and may be from 1 to 90 wt %, preferably from 5 to 90 wt %, and more preferably from 10 to 70 wt % for a propylene copolymer.

The cyclic olefin may include 3 to 24 carbon atoms, and may preferably include 3 to 18 carbon atoms. Particularly, cyclopentene, cyclobutene, cyclehexene, 3-methylcyclohexene, cyclooctene, tetracyclodecene, octacyclodecene, dicyclopentadiene, norbornene, 5-methyl-2-norbornene, 5-ethyl-2-norbornene, 5-isobutyl-2-norbornene, 5,6-dimethyl-2-norbornene, 5,5,6-trimethyl-2-norbornene and ethylenenorbornene may be used. The cyclic olefin may be copolymerized with the alpha-olefin, and in this case, the amount of the cyclic olefin may be from 1 to 50 wt % and may preferably be 2 to 50 wt % with respect to a copolymer.

In addition, the diene and triene may be a polyene having two or three double bonds and 4 to 26 carbon atoms. Particularly, 1,3-butadiene, 1,4-pentadiene, 1,4-hexadiene, 1,5-hexadiene, 1,9-decadiene, 2-methyl-1,3-butadidne, etc. may be used. The styrene may preferably be styrene or styrene substituted with an alkyl group having 1 to 10 carbon atoms, an alkoxy group having 1 to 10 carbon atoms, a halogen group, an amine group, a silyl group, a halogenated alkyl group, etc.

According to another embodiment, the polymerization step may be performed in a hydrocarbon solvent via solution phase, slurry phase, bulk phase or gas phase polymerization.

The catalyst composition may have a homogeneous solution state, a supported state on a support or an insoluble particle state of a support, and so, the polymerization may be performed via the solution phase, the slurry phase, the bulk phase or the gas phase polymerization. In addition, polymerization conditions of each polymerization method may be diversely modified according to the state of a catalyst (homogeneous phase or inhomogeneous phase (supported type)), a polymerization method (solution polymerization, slurry polymerization, gas polymerization), target polymerization result or a polymer type. The modification degree may be easily determined by an expert in this field.

The hydrocarbon solvent dissolved or diluted in an aliphatic hydrocarbon solvent having 5 to 12 carbon atoms such as pentane, hexane, heptane, nonane, decane and an isomer thereof, an aromatic hydrocarbon solvent such as toluene and benzene, or a hydrocarbon solvent substituted with a chlorine atom such as dichloromethane and chlorobenzene, may be used alone or as a mixture of at least two thereof and injected. At least one of the solvent dissolved or diluted may be mixed and injected. The solvent used may preferably be treated with a small amount of alkylaluminum to remove a trace amount of water or air functioning as a catalytic poison, and a promotor may be further included.

The alkylaluminum may include, for example, trialkylaluminum, dialkyl aluminum halide, alkyl aluminum dihalide, aluminum dialkyl hydride or alkyl aluminum sesqui halide, etc. More particularly, $Al(C_2H_5)_3$, $Al(C_2H_5)_2H$, $Al(C_3H_7)_3$, $Al(C_3H_7)_2H$, $Al(i-C_4H_9)_2H$, $Al(C_8H_{17})_3$, $Al(C_{12}H_{25})_3$, $Al(C_2H_5)(C_{12}H_{25})_2$, $Al(i-C_4H_9)(C_{12}H_{25})_2$, $Al(i-C_4H_9)_2H$, $Al(i-C_4H_9)_3$, $(C_2H_5)_2AlCl$, $(i-C_3H_9)_2AlCl$ or $(C_2H_5)_3Al_2Cl_3$ etc. may be used. These organic aluminum compounds may be continuously inserted in each reactor and may be inserted by the molar ratio from about 0.1 to 10 mol per 1 kg of a reaction medium inserted in the reactor to remove water appropriately.

According to another embodiment, the polymerization step may be performed in a batch type reactor or a continuous type reactor, and may be preferably performed in a continuous type reactor.

According to another embodiment, the polymerization step may be performed in the presence of an inert gas such as an argon gas or a nitrogen gas.

The inert gas may be, for example, a nitrogen gas or a hydrogen gas alone or a mixture thereof.

By using the inert gas, the suppression of the catalyst activity due to the injection of water or impurities in the air may be prevented. The amount ratio of the inert gas:the olefin-based monomer inserted may be from about 1:10 to about 1:100, without limitation. In the case that the amount of the inert gas is excessively small, the reaction of the catalyst composition may be violent, and the preparation of the olefin-based polymer having molecular weight and molecular weight distribution may become difficult. In the case that an excessive amount of the inert gas is inserted, the activity of the catalyst composition may be insufficiently attained.

The polymerization temperature during copolymerizing the ethylene and the alpha-olefin as a comonomer using the catalyst may be from about 130 to about 250° C., and may preferably be from about 140 to about 200° C.

In addition, the polymerization pressure may preferably be from about 1 to about 150 bar, may more preferably be from about 1 to about 120 bar, and most preferably be from about 10 to about 120 bar.

According to an embodiment, there is provided an olefin-based polymer prepared by the above-described method of preparing an olefin-based polymer.

According to an embodiment, there is provided an olefin-based polymer in which at least two polyolefin units having different crystallinity are mixed.

According to another embodiment, in TREF, the olefin-based polymer may have a peak for a first semicrystalline olefin-based polymer (P1) and a peak for a second semicrystalline olefin-based polymer (P2).

The peak for the first semicrystalline olefin-based polymer has lower density and lower elution temperature Te1 than the peak for the second semicrystalline olefin-based polymer. The peak for the second semicrystalline olefin-based polymer has relatively higher density and higher elution temperature Te2 than the peak for the first semicrystalline olefin-based polymer.

According to another embodiment, the olefin-based polymer may be used for hollow molding, extrusion molding or injection molding.

MODE FOR CARRYING OUT THE INVENTION

Hereinafter, the present invention will be explained in particular with reference to the following examples. However, the following examples are illustrated to assist the understanding of the present invention, and the scope of the present invention is not limited thereto.

Synthesis of Ligand and Transition Metal Compound

Organic reagents and solvents were purchased from Aldrich Co. and purified by a standard method unless otherwise specifically stated. In all synthetic steps, the contact of the air and moisture were blocked to improve the reproducibility of experiments.

Preparation Example 1

A compound of 8-(1,2-dimethyl-1H-benzo[b]cyclopenta[d]thiophen-3-yl)-2-methyl-1,2,3,4-tetrahydroquinoline

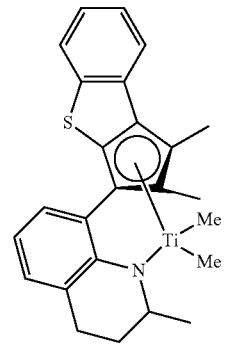

n-BuLi (14.9 mmol, 1.1 eq) was slowly added drop by drop in a solution of 2-methyl-1,2,3,4-tetrahydroquinoline (2 g, 13.6 mmol) dissolved in 10 mL of ether at −40° C. The temperature was slowly elevated to room temperature, and the reaction mixture was stirred at room temperature for 4 hours. The temperature was lowered to −40° C. again and $CO_2$ (g) was inserted, and the reaction was maintained for 0.5 hours at a low temperature. The temperature was slowly elevated, and remaining $CO_2$ (g) was removed via a bubbler. THF (17.6 mmol, 1.4 ml) and t-BuLi(10.4 mmol, 1.3 eq) were inserted in the reaction mixture at −20° C., following by aging at a low temperature at −20° C. for 2 hours. The ketone (1.9 g, 8.8 mmol) was dissolved in diethyl ether and slowly added drop by drop in the reaction mixture. After stirring at room temperature for 12 hours, 10 mL of water was inserted and hydrochloric acid (2N, 60 mL) was added in the reactant, followed by stirring for 2 minutes. Organic solvents were extracted and the reactant was neutralized with a $NaHCO_3$ aqueous solution. Then, the organic solvent was extracted and dried with $MgSO_4$. Through silica gel column chromatography, an yellow oil (1.83 g, 60% yield) was obtained.

1H NMR (C6D6): δ 1.30 (s, 3H, CH3), 1.35 (s, 3H, CH3), 1.89-1.63 (m, 3H, Cp-H quinoline-CH2), 2.62-2.60 (m, 2H, quinoline-CH2), 2.61-2.59 (m, 2H, quinoline-NCH2), 2.70-2.57 (d, 2H, quinoline-NCH2), 3.15-3.07 (d, 2H, quinoline-NCH2), 3.92 (broad, 1H, N—H), 6.79-6.76 (t, 1H, aromatic), 7.00-6.99 (m, 2H, aromatic), 7.30-7.23 (m, 2H, aromatic), 7.54-7.53 (m, 1H, aromatic), 7.62-7.60 (m, 1H, aromatic) ppm A compound of 8-(1,2-dimethyl-1H-benzo[b]cyclopenta[d]thiophen-3-yl)-2-methyl-1,2,3,4-tetrahydroquinoline-titanium dichloride n-BuLi (3.0 mmol, 2.1 eq) was slowly added drop by drop in the ligand (1.0 g, 2.89 mmol) at −20° C. The formation of an yellow slurry was observed, and the temperature was slowly elevated to room temperature, followed by stirring at room temperature for 12 hours. TiCl4DME (806 mg, 2.89 mmol, 1.0 eq) was added drop by drop, followed by stirring at room temperature for 12 hours. After removing solvents, the reactant was extracted with toluene to obtain a red solid (700 mg, 52% yield).

1H NMR (C6D6): δ 1.46-1.467 (t, 2H, quinoline-NCH2), 1.85 (s, 3H, Cp-CH3), 1.79 (s, 3H, Cp-CH3), 2.39 (s, 3H, Cp-CH3), 2.37 (s, 3H, Cp-CH3), 2.10-2.07 (t, 2H, quinoline-NCH2), 5.22-5.20 (m, 1H, N—CH), 5.26-5.24 (m, 1H, N—CH), 6.89-6.87 (m, 2H, aromatic) 6.99~6.95 (m, 1H, aromatic), 7.19-7.08 (m, 2H, aromatic), 7.73-7.68 (m, 1H, aromatic) ppm Preparation of Olefin Polymer Example 1

In a 1.5 L autoclave continuous process reactor, a hexane solvent (5.1 kg/h) and 1-butene (0.92 kg/h) were added, and the temperature of the upper end portion of the reactor was pre-heated to 160° C. A triisobutylaluminum compound (0.05 mmol/min), the metallocene compound thus obtained (0.5 μmol/min) and dimethylanilinium tetrakis(pentafluorophenyl)borate promotor (1.5 μmol/min) were added in the reactor at the same time. Then, ethylene (0.87 kg/h) was inserted in the autoclave reactor, and the reaction mixture was maintained under the pressure of 89 bar at 160° C. for 30 minutes, and a copolymerization reaction was performed in a continuous process to produce a copolymer. After that, a remaining ethylene gas was exhausted, and a polymer solution was dried in a vacuum oven and dried for at least 12 hours. Then, physical properties thereof were measured.

Example 2

An olefin-based polymer was prepared by the same procedure described in the above Example 1 except for using 1-octene (0.92 kg/h) instead of 1-butene.

Example 3

An olefin-based polymer was prepared by the same procedure described in the above Example 1 except for using 1-octene (1.2 kg/h) instead of 1-butene.

Example 4

An olefin-based polymer was prepared by the same procedure described in the above Example 1 except for using 1-butene (1.13 kg/h).

Example 5

An olefin-based polymer was prepared by the same procedure described in the above Example 1 except for using 1-octene (1.6 kg/h) instead of 1-butene.

Example 6

An olefin-based polymer was prepared by the same procedure described in the above Example 1 except for using 1-butene (0.9 kg/h).

Example 7

An olefin-based polymer was prepared by the same procedure described in the above Example 1 except for using 1-octene (1.2 kg/h) instead of 1-butene, and setting the temperature of the reactor to 180° C.

Comparative Example 1

An ethylene-1-butene copolymer of Dow Co. (trade name; HM7387) prepared by using only one kind of a metallocene catalyst was prepared.

Comparative Example 2

An ethylene-1-octene copolymer of LG Chem. Ltd. (trade name; LC670) prepared by using only one kind of a metallocene catalyst was prepared.

Comparative Example 3

An ethylene-1-octene copolymer of LG Chem. Ltd. (trade name; LC760) prepared by using only one kind of a metallocene catalyst was prepared.

Comparative Example 4

An olefin polymer was prepared by the same procedure described in the above Example 1 except for using a mixture of a first metallocene compound ([(1,2,3,4-tetrahydroquinolin-8-yl)tetramethylcyclopentadienyl-eta5,kappa-N]titanium dimethyl) and a second metallocene compound ([methyl(6-t-butoxyhexyl)silyl(η5-tetramethylCp)(t-butylamido)]TiCl2 compound) and using 1-butene (0.90 kg/h).

Comparative Example 5

An olefin polymer was prepared by the same procedure described in the above Example 1 except for using a mixture of a first metallocene compound ([(1,2,3,4-tetrahydroquinolin-8-yl)tetramethylcyclopentadienyl-eta5,kappa-N]titanium dimethyl) and a second metallocene compound ([methyl(6-t-butoxyhexyl)silyl(η5-tetramethylCp)(t-butylamido)]TiCl2 compound) and using 1-octene (1.30 kg/h) instead of 1-butene.

Comparative Example 6

An olefin polymer was prepared by the same procedure described in the above Example 1 except for using a mixture of a first metallocene compound ([(1,2,3,4-tetrahydroquinolin-8-yl)tetramethylcyclopentadienyl-eta5,kappa-N]titanium dimethyl) and a second metallocene compound ([methyl(6-t-butoxyhexyl)silyl(η$^5$-tetramethylCp)(t-butylamido)]TiCl$_2$ compound) and using 1-octene (1.63 kg/h) instead of 1-butene.

Experimental Example 1

Measuring TREF

TREF was measured by using a TREF machine of PolymerChar and an o-dichlorobenzene solvent in a range of −20-130° C.

80 mg of a polymer sample was dissolved in 20 ml of an o-dichlorobenzene solvent at 135° C. for 30 minutes and stabilized at 95° C. for 30 minutes. The solution thus obtained was introduced in a TREF column, cooled to −20° C. by the temperature decreasing rate of 0.5° C./min, and supported for 2 minutes. Then, the temperature was increased from −20° C. to 130° C. by the temperature increasing rate of 1° C./min, and the concentration of an eluted polymer was measured while flowing the o-dichlorobenzene solvent in the column by the flowing rate of 0.5 mL/min.

Figure 2:
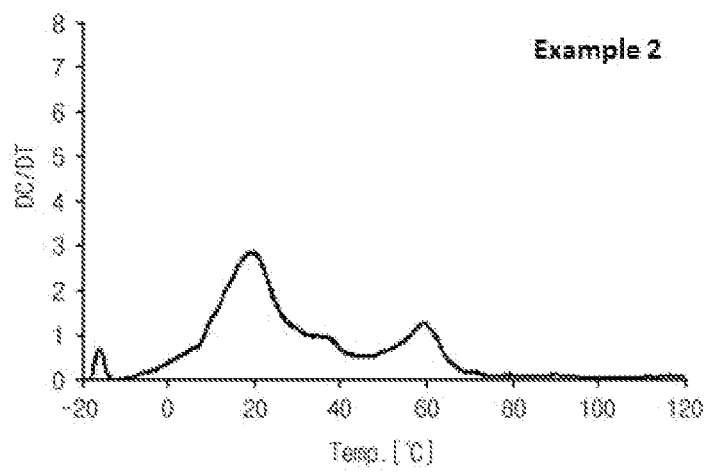
FIG. 2 illustrates a TREF graph of an olefin-based polymer prepared in Example 2.
Figure 3:
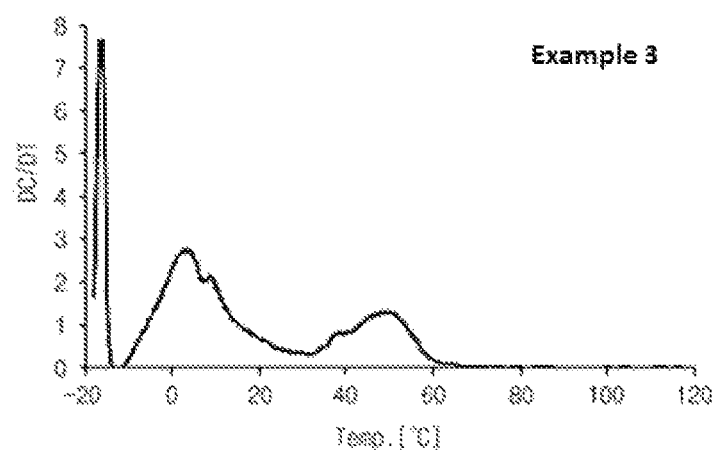
FIG. 3 illustrates a TREF graph of an olefin-based polymer prepared in Example 3.
Figure 4:
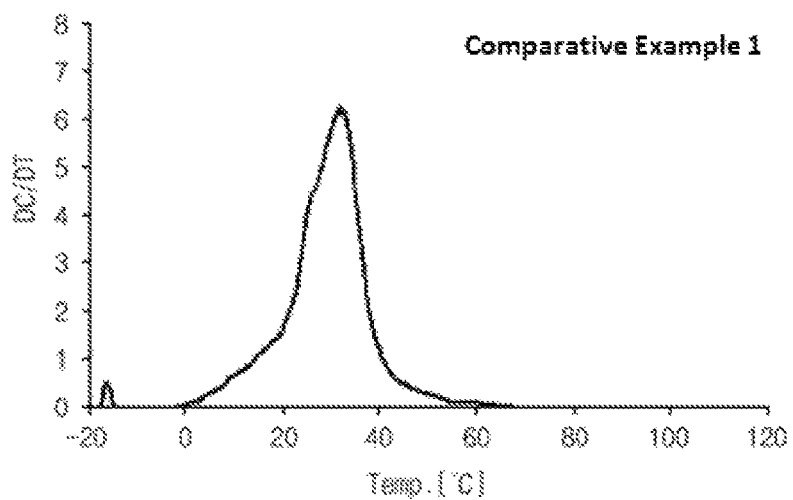
FIG. 4 illustrates a TREF graph of an olefin-based polymer prepared in Comparative Example 1.
Figure 5:
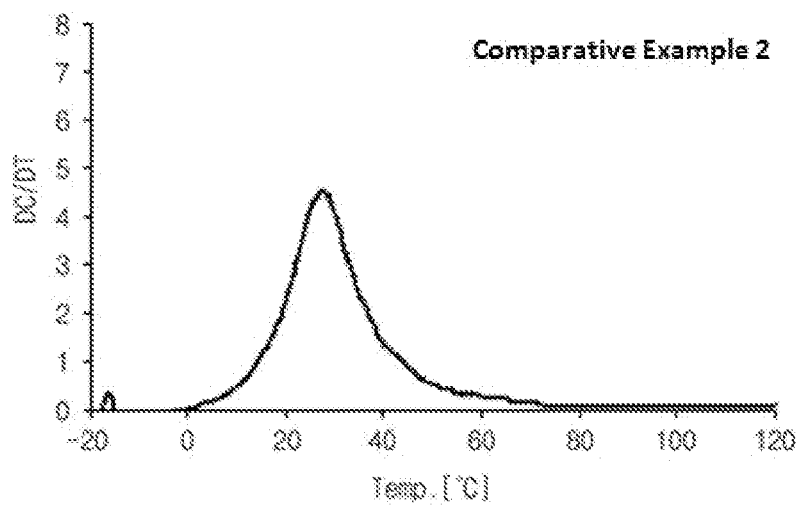
FIG. 5 illustrates a TREF graph of an olefin-based polymer prepared in Comparative Example 2.
Figure 6:
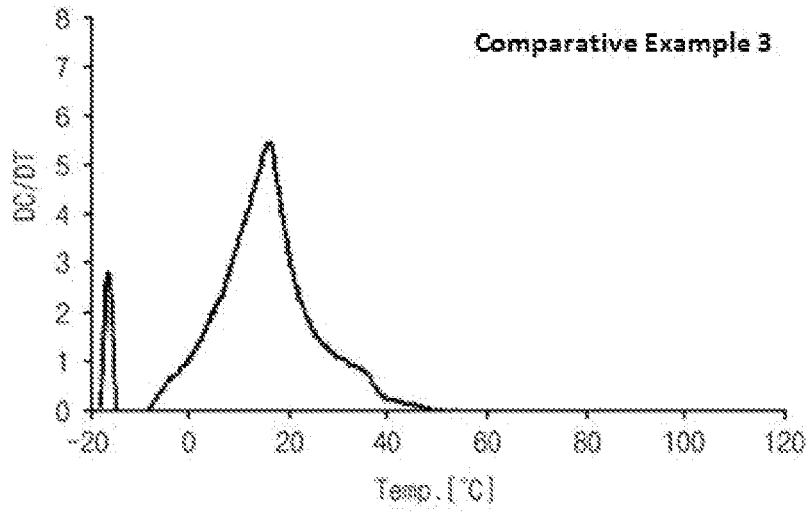
FIG. 6 illustrates a TREF graph of an olefin-based polymer prepared in Comparative Example 3.
Figure 7:
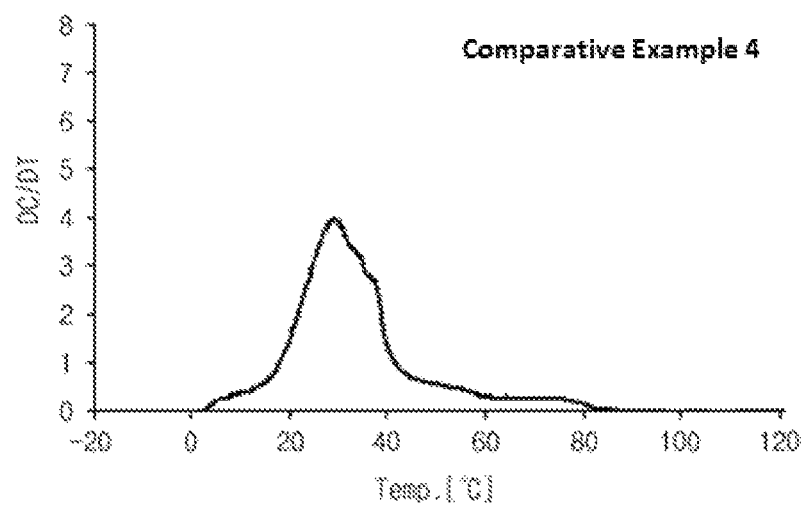
FIG. 7 illustrates a TREF graph of an olefin-based polymer prepared in Comparative Example 4.
Figure 8:
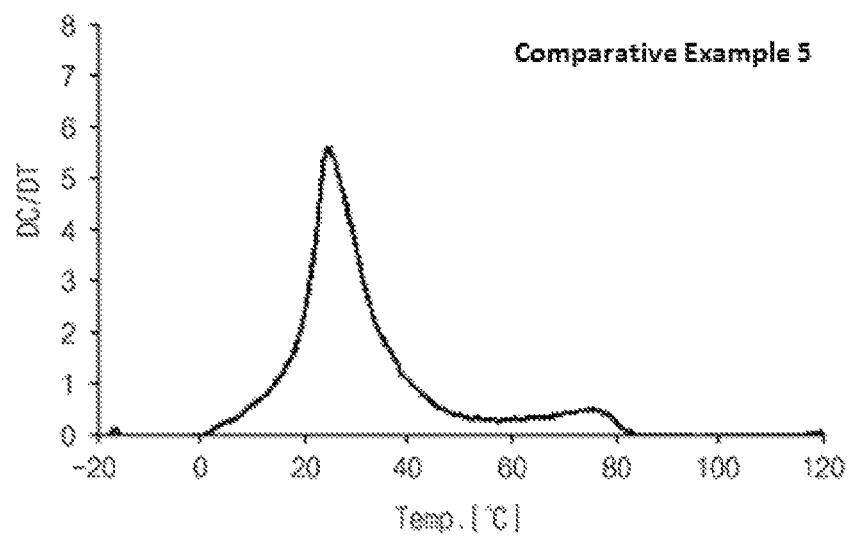
FIG. 8 illustrates a TREF graph of an olefin-based polymer prepared in Comparative Example 5.
Figure 9:
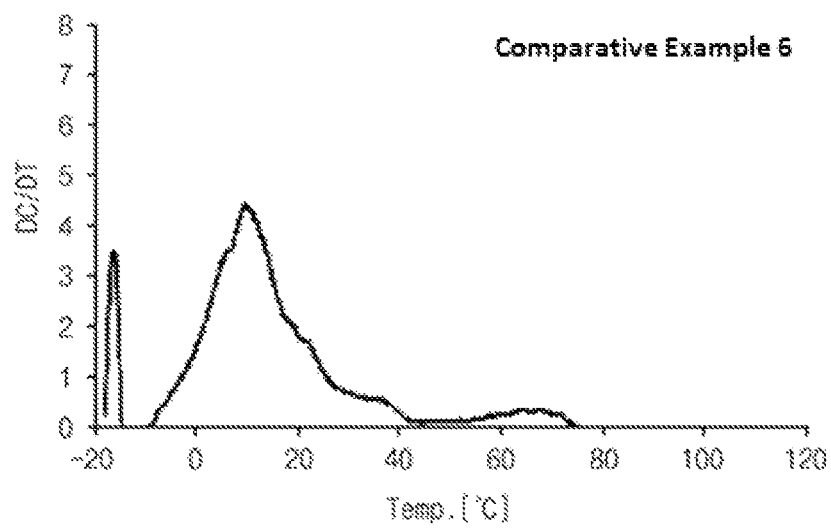
FIG. 9 illustrates a TREF graph of an olefin-based polymer prepared in Comparative Example 6.

The measured results of TREF are illustrated in FIGS. 1 to 9 and the following Table 1.

Experimental Example 2

Measuring BGN

BGN may be obtained by continuously measuring molecular weight, molecular weight distribution and the branch amount at the same time by using a GPC-FTIR apparatus or a CFC apparatus and then calculating using Equation 1.

The molecular weight, the molecular weight distribution and the branch amount were measured at the same time by using the GPC-FTIR apparatus or the CFC apparatus. A molecular weight curve was drawn while setting the log value (log Mw) of the molecular weight (Mw) to the x-axis, and the molecular weight distribution with respect to the log value (dwt/dlog Mw) to the y-axis. Both end parts at the left and right sides of the graph by 10% were respectively excluded from the total area, and the branch amount (unit: number/1,000 C) of low molecular weight was obtained at the left border of the remaining 80% in the middle area, and the branch amount of high molecular weight was obtained at the right border of the remaining 80% in the middle area. BGN may be obtained by calculating using the following Equation 1.

[Equation 1]

$$\text{Branch Gradient Number}(BGN) = \frac{(\text{Branch amount of high molecular weight} - \text{Branch amount of low molecular weight})}{(\text{Branch amount of low molecular weight})}$$

In the above Equation 1, the low molecular weight means the molecular weight of bottom 10%, and the high molecular weight means the molecular weight of top 10% in total molecular weight distribution, and the branch amount means the amount of a branch having at least two carbon atoms per 1,000 carbon atoms.

Experimental Example 3

Measuring Other Physical Properties

Density of a polymer; measured by ASTM D-792.

Molecular weight distribution; obtained by measuring number average molecular weight (Mn) and weight average molecular weight (Mw) using gel permeation chromatography (GPC), and dividing the weight average molecular weight by the number average molecular weight.

MI of a polymer was measured by ASTM D-1238 (Condition E, 190° C., 2.16 kg weight).

Experimental Example 4

Measuring DSC

DSC was obtained by using Differential Scanning calorimeter 6000 manufactured by PerKinElmer Co. That is, the temperature was elevated to 200° C., this temperature was maintained for 1 minute, the temperature was decreased to −100° C., and the temperature was elevated again. The apex of a DSC curve was melting temperature. In this case, the temperature increasing and decreasing rates were 10° C./min, and the melting temperature was obtained during the second elevation of the temperature. The DSC analysis results of the polymer according to the present invention are illustrated in the following Table 1.

TABLE 1

| Sample Unit | density g/cc | MI 2.16 g/10 min | Tm1 °C. | Tm2 °C. | Mw | MWD | Te1 °C. | Te2 °C. | P1 % | P2 % | BGN |
|---|---|---|---|---|---|---|---|---|---|---|---|
| Comparative Example 1 | 0.872 | 0.27 | 49.1 | — | 163099 | 2.31 | 30.4 | — | 100 | — | −0.006 |
| Comparative Example 2 | 0.869 | 5.1 | 56.9 | — | 107847 | 2.44 | 23.6 | — | 100 | — | 0.006 |
| Comparative Example 3 | 0.862 | 11.0 | 48.9 | — | 96230 | 2.41 | 15.6 | — | 100 | — | 0.004 |
| Comparative Example 4 | 0.870 | 0.38 | 52.3 | 99.5 | 129631 | 2.34 | 28.0 | 71.4 | 93.5 | 6.5 | 0.020 |
| Comparative Example 5 | 0.872 | 5.1 | 56.1 | 100.6 | 98993 | 2.51 | 23.6 | 74 | 91.7 | 8.3 | 0.060 |
| Comparative Example 6 | 0.863 | 11.1 | 40.8 | 96.1 | 84514 | 2.52 | 7.0 | 68.6 | 91.8 | 8.2 | 0.053 |
| Example 1 | 0.873 | 0.23 | 34.0 | 82.4 | 162989 | 2.26 | 13.4 | 58.2 | 70.3 | 29.7 | −0.050 |

TABLE 1-continued

| Sample Unit | density g/cc | MI 2.16 g/10 min | Tm1 °C. | Tm2 °C. | Mw | MWD | Te1 °C. | Te2 °C. | P1 % | P2 % | BGN |
|---|---|---|---|---|---|---|---|---|---|---|---|
| Example 2 | 0.870 | 3.2 | 46.3 | 85.2 | 117975 | 2.36 | 16.6 | 57.4 | 75.9 | 24.1 | −0.043 |
| Example 3 | 0.861 | 10.8 | 20.0 | 75.2 | 98328 | 2.21 | 2.8 | 47.4 | 74.0 | 26.0 | −0.044 |

As shown in the above Table 1, the olefin-based polymers according to the present invention exhibit two peaks of P1 and P2 during measuring TREF and has two Te, i.e., Te1 and Te2, different from the olefin-based polymers of Comparative Examples 1, 2 and 3.

Meanwhile, the olefin-based polymers of Examples 1 to 3 using a single catalyst according to the examples of the present invention have a negative value of BGN and in the range from −1.0 to −0.001, different from the olefin-based polymers of Comparative Examples 4, 5 and 6 using two kinds of metallocene catalysts. When the BGN is in the range as in the examples of the present invention, the physical properties such as the tensile strength and elongation of a base resin may be increased.

In addition, the olefin-based polymers of Examples 1 to 3 according to the present invention show two Tms according to the analysis result of DSC, different from the olefin-based polymers of Comparative Examples 1, 2 and 3.

In addition, the olefin-based polymers of Examples 1 to 3 using a single catalyst according to the examples of the present invention have two Tms and narrow molecular weight distribution (MWD) in a range from 2.2 to 2.4, different from the olefin-based polymers of Comparative Examples 4, 5 and 6 using two kinds of metallocene catalysts.

The following Table 2 illustrates measured results of the change of Te1 and Te2 according to the addition amount of 1-butene or 1-octene, which is a comonomer.

TABLE 2

| Sample unit | density g/cc | MI 2.16 g/10 min | Te1 °C. | Te2 °C. |
|---|---|---|---|---|
| Example 4 | 0.870 | 0.65 | 1.8 | 50.4 |
| Example 5 | 0.875 | 1.80 | 25.6 | 63.8 |
| Example 6 | 0.885 | 0.64 | 33.2 | 65.4 |
| Example 7 | 0.885 | 0.03 | 42.4 | 70.6 |

As shown in the above Table 2, the olefin-based polymers of Examples 4 to 7 according to the present invention show two Te when measuring TREF. In a density range from about 0.870 to about 0.885 g/cc, the Te1 is shown in a temperature range from about 1.8 to about 42.4° C., and the Te2 is shown in a temperature range from about 50.4 to about 70.6° C.

Thus, it would be found that the Te1 and the Te2 may be affected by the addition amount of the comonomer.

INDUSTRIAL APPLICABILITY

The olefin-based polymer according to the present invention has narrow molecular weight distribution, includes two Te1 and Te2 when measuring TREF, and shows a specific BGN value, and thus, may exhibit excellent tensile strength and elongation. Therefore, the olefin-based polymer may be used in diverse fields and uses including wrapping, construction, daily supplies, etc. such as a material of an automobile, a wire, a toy, a fiber, a medicine, etc.

The invention claimed is:

1. An olefin-based polymer including an elution temperature 1 (Te1) and an elution temperature 2 (Te2), which are elution temperatures of the olefin-based polymer in a temperature range from −20° C. to 130° C. when measuring temperature rising elution fractionation (TREF), and
    having branch gradient number (BGN) from −1.0 to −0.001 when measuring chromatography Fourier transform infrared spectroscopy (GPC FT-IR).

2. The olefin-based polymer of claim 1, wherein the Te1 is present at relatively lower temperature than the Te2 when measuring the TREF, and
    the Te1 is in a range from −20° C. to 100° C., and the Te2 is in a range from 0° C. to 120° C. in a density range from 0.85 to 0.91 g/cc of the olefin-based polymer.

3. The olefin-based polymer of claim 2, wherein the Te1 is in a range from −20° C. to 30° C., and the Te2 is in a range from 30° C. to 80° C. in a density range from 0.85 to 0.87 g/cc of the olefin-based polymer.

4. The olefin-based polymer of claim 2, wherein the Te1 is in a range from 10° C. to 50° C., and the Te2 is in a range from 50° C. to 100° C. in a density range from 0.87 to 0.89 g/cc of the olefin-based polymer.

5. The olefin-based polymer of claim 2, wherein the Te1 is in a range from 20° C. to 70° C., and the Te2 is in a range from 70° C. to 120° C. in a density range from 0.89 to 0.91 g/cc of the olefin-based polymer.

6. The olefin-based polymer of claim 1, wherein the olefin-based polymer comprises a first semicrystalline olefin-based polymer and a second semicrystalline olefin-based polymer, and
    a fraction ratio of a peak for the first semicrystalline olefin-based polymer (P1) is 5 to 95%, and a fraction ratio of a peak for the second semicrystalline olefin-based polymer (P2) is 5 to 95% when measuring TREF.

7. The olefin-based polymer of claim 6, wherein the fraction ratio of the peak for the first semicrystalline olefin-based polymer (P1) is 10 to 90%, and the fraction ratio of the peak for the second semicrystalline olefin-based polymer (P2) is 10 to 90% when measuring TREF.

8. The olefin-based polymer of claim 1, wherein the BGN is from −0.8 to −0.001.

9. The olefin-based polymer of claim 1, wherein the olefin-based polymer comprises Tm1 and Tm2, which are melting temperatures (Tm) obtained in a differential scanning calorimetry (DSC) graph obtained by measuring DSC, and
    the Tm1 is in a range from −30 to 120° C., and the Tm2 is in a range from −10 to 140° C. in a density range from 0.85 to 0.91 g/cc of the olefin-based polymer.

10. The olefin-based polymer of claim 9, wherein the Tm1 is in a range from −30 to 45° C., and the Tm2 is in a range from 45 to 110° C. in a density range from 0.85 to 0.87 g/cc of the olefin-based polymer.

11. The olefin-based polymer of claim 9, wherein the Tm1 is in a range from 20 to 75° C., and the Tm2 is in a range from 75 to 120° C. in a density range from 0.87 to 0.89 g/cc of the olefin-based polymer.

12. The olefin-based polymer of claim 9, wherein the Tm1 is in a range from 30 to 90° C., and the Tm2 is in a range from 90 to 140° C. in a density range from 0.89 to 0.91 g/cc of the olefin-based polymer.

13. The olefin-based polymer of claim 1, wherein melting index (MI) of the olefin-based polymer is from 0.1 to 2,000 g/10 min.

14. The olefin-based polymer of claim 1, wherein weight average molecular weight (Mw) of the olefin-based polymer is from 10,000 to 500,000 g/mol.

15. The olefin-based polymer of claim 1, wherein molecular weight distribution (MWD) of the olefin-based polymer is from 1.0 to 3.0.

16. The olefin-based polymer of claim 1, wherein the olefin-based polymer is for hollow molding, extrusion molding or injection molding.

17. The olefin-based polymer of claim 1, wherein the olefin-based polymer is obtained by polymerizing an olefin-based monomer using a catalyst composition comprising a transition metal compound represented by the following Formula 1:

[Formula 1]

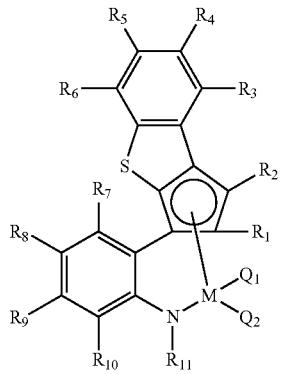

in the above Formula 1,

M is a transition metal in group 4, $Q_1$ and $Q_2$ are the same or different and independently hydrogen; halogen; alkyl having 1 to 20 carbon atoms; alkenyl having 2 to 20 carbon atoms; aryl having 6 to 20 carbon atoms; alkylaryl having 6 to 20 carbon atoms; arylalkyl having 7 to 20 carbon atoms; alkyl amido having 1 to 20 carbon atoms; aryl amido having 6 to 20 carbon atoms; or alkylidene having 1 to 20 carbon atoms, $R_1$ to $R_6$ are the same or different and independently hydrogen; silyl; alkyl having 1 to 20 carbon atoms; alkenyl having 2 to 20 carbon atoms; aryl having 6 to 20 carbon atoms; alkylaryl having 7 to 20 carbon atoms; arylalkyl having 7 to 20 carbon atoms; or a metalloid radical of a metal in group 14 substituted with hydrocarbyl having 1 to 20 carbon atoms; $R_1$ and $R_2$ may be connected from each other, or at least two of $R_3$ to $R_6$ may be connected to each other to form an aliphatic ring having 5 to 20 carbon atoms or an aromatic ring having 6 to 20 carbon atoms; the aliphatic ring or the aromatic ring may be substituted with halogen, alkyl having 1 to 20 carbon atoms, alkenyl having 2 to 20 carbon atoms or aryl having 6 to 20 carbon atoms, $R_7$ to $R_{11}$ are the same or different and independently hydrogen; alkyl having 1 to 20 carbon atoms; alkenyl having 2 to 20 carbon atoms; aryl having 6 to 20 carbon atoms; alkylaryl having 7 to 20 carbon atoms; or arylalkyl having 7 to 20 carbon atoms; at least two adjacent to each other of $R_7$ to $R_{11}$ may be connected to each other to form an aliphatic ring having 5 to 20 carbon atoms or an aromatic ring having 6 to 20 carbon atoms; the aliphatic ring or the aromatic ring may be substituted with halogen, alkyl having 1 to 20 carbon atoms, alkenyl having 2 to 20 carbon atoms or aryl having 6 to 20 carbon atoms.

* * * * *